United States Patent
DeGeorge et al.

(10) Patent No.: US 9,265,717 B1
(45) Date of Patent: Feb. 23, 2016

(54) COMPOSITIONS COMPRISING CATALASE-PEROXIDASE AND METHODS FOR ALTERING THE COLOR OF HAIR

(71) Applicant: L'Oreal, Paris (FR)

(72) Inventors: Michael DeGeorge, Old Bridge, NJ (US); Mark Benn, Union, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/573,578

(22) Filed: Dec. 17, 2014

(51) Int. Cl.
*A61Q 5/10* (2006.01)
*A61K 8/00* (2006.01)
*A61K 8/97* (2006.01)
*A61K 8/23* (2006.01)
*A61K 8/49* (2006.01)
*A61K 8/66* (2006.01)

(52) U.S. Cl.
CPC ... *A61K 8/97* (2013.01); *A61K 8/23* (2013.01); *A61K 8/4973* (2013.01); *A61K 8/66* (2013.01); *A61Q 5/10* (2013.01); *A61K 2800/522* (2013.01); *C12Y 111/01021* (2013.01)

(58) Field of Classification Search
CPC ............. A61Q 5/10; A61K 8/23; A61K 8/97; C12Y 111/01021
USPC ........................................... 8/405; 424/70.14
See application file for complete search history.

(56) References Cited

U.S. PATENT DOCUMENTS

2009/0169651 A1* 7/2009 Majeed .................... A61K 8/97 424/727

OTHER PUBLICATIONS

English translation (6/3015) of the Patent No. CN 1017155997.*

* cited by examiner

*Primary Examiner* — Eisa Elhilo
(74) *Attorney, Agent, or Firm* — The Marbury Law Group, PLLC

(57) ABSTRACT

Disclosed are compositions and methods for controlling or slowing down the coloration of keratin fibers such as hair involving providing compositions comprising coconut water which contains catalase-peroxidase and at least one antioxidant, wherein the pH of the composition is from about 2 to about 6.

21 Claims, No Drawings

COMPOSITIONS COMPRISING CATALASE-PEROXIDASE AND METHODS FOR ALTERING THE COLOR OF HAIR

TECHNICAL FIELD

The present disclosure relates to compositions for controlling the coloration process on keratin substrates, for instance human keratin fibers such as the hair, comprising providing a composition comprising coconut water which contains catalase-peroxidase and at least one antioxidant.

BACKGROUND OF THE INVENTION

It is known that consumers desire to use cosmetic and personal care compositions that enhance the appearance of keratin fibers such as hair by changing the color of the hair and/or by imparting various properties to hair such as shine and conditioning. The process of changing the color of hair can involve either depositing an artificial color onto the hair which provides a different shade or color to the hair or lifting the color of the hair, such as for example, from a dark brown shade to a medium brown or a light brown shade.

However, there are difficulties presented with obtaining consistent and uniform color on hair when consumers dye or alter the color of their hair. For example, the hair will grow out, creating a visible demarcation line between the regrowth of the roots and the last dye session. Artificial color on hair also has the tendency to fade over time, especially during the shampooing process, resulting in a dull or matte look to the hair fiber. Furthermore, the processing times for hair color compositions vary greatly for undyed virgin hair (not chemically processed hair) and heavily colored or chemically processed hair. The level of skill required to preserve the condition of overly colored and processed hair when applying a fresh coat of hair color while also maintaining a uniform shade of color from root to tip is very high.

It has now been discovered that by providing an acidic hair pretreatment composition comprising coconut water and at least one antioxidant, it is possible to form a film or coating on a substrate that has certain desirable properties, such as a protective barrier that will control or slow down the coloration process. Said compositions may be used prior to dyeing to either enhance or reduce the dye penetration into the fiber. Said compositions may also be applied on overly chemically processed hair before coloring or altering the color of the hair in order to preserve the condition of the hair and to also provide a uniform color of the hair from the root to the tip. In particular, the compositions can be used in re-coloring or re-dyeing the hair. Typically, a visible demarcation line at a point along the shaft of artificially colored hair can be observed as new hair grows out from the roots. As the hair grows out, the color of the hair from the demarcation line down the length of the hair is generally different from the color of the new hair. Accordingly, the hair pretreatment compositions of the invention, that aid in the uniform distribution of coloring agents onto the hair fiber or in obtaining uniformly colored hair along the length of the hair fiber or in satisfactory gray hair coverage can be useful in increasing the efficiency of hair coloring agents and/or of hair coloring processes.

In addition, applying the acidic pretreatment composition of the present invention onto hair in order to create a barrier or coating on hair may also be useful in highlighting, lowlighting, and bleaching of hair. Such a barrier or coating allows the selective coloration or alteration of the color of portions of hair while leaving other portions of hair unchanged and/or uncolored, resulting in color alterations only in selected portions of the hair. Accordingly, the acidic hair pretreatment compositions of the invention can also aid in achieving a multi-toned or multi-colored or highlighted or lowlighted hair in a more convenient and easy manner.

Surprisingly and unexpectedly, the inventors have discovered that using an acidic pretreatment composition on hair before coloring or altering the color of the hair wherein the composition comprises coconut water and at least one antioxidant resulted in a method for controlling or slowing down the coloration of the hair in order to allow for more uniform hair coloring. The current invention allows for easy and improved coloration of the hair fibers to get a uniform hair color from root to ends of the hair. When applied starting from the visible demarcation line which is generally in the middle of the hair shaft (mid-shaft) down the length of artificially colored hair, the pretreatment composition of the invention will create a barrier or coating on the hair to impede a subsequent hair color altering or hair coloring composition from penetrating into the shaft as fast as it would without the pretreatment composition on the hair.

BRIEF SUMMARY OF THE INVENTION

The present invention relates to an acidic hair pretreatment composition for controlling or slowing down the coloration of hair, the composition comprising:
  a) from about 10% to about 80% by weight of active material, of coconut water;
  b) from about 0.5% to about 20% by weight of at least one antioxidant;
  c) optionally, at least one cosmetically acceptable carrier; and
wherein the pH of the composition is from about 2 to about 6; all weights being relative to the total weight of the composition.

The present invention also relates to methods for controlling or slowing down the coloration of hair involving applying onto hair, the above-described acidic pretreatment composition, followed by the application of a hair color altering composition.

DETAILED DESCRIPTION OF THE INVENTION

It has been unexpectedly and surprisingly discovered that the compositions and methods of the present invention provide hair color benefits onto keratin fibers such as hair which allow for more uniform hair coloring.

Without being bound by theory, it is believed that combinations of a coconut water and at least one antioxidant in an acidic system provide compositions that impart films or coatings on the surface of keratin fibers such as hair which inhibit, reduce or enhance color deposit, thereby creating equal or uniform deposit of hair color from the roots to the ends of the hair shaft.

The composition of the present invention is particularly useful as a hair pretreatment composition.

As used herein, the expression "at least one" means one or more and thus includes individual components as well as mixtures/combinations.

It is also to be understood that, as used herein the terms "the," "a," or "an," mean "at least one," are understood to encompass the plural as well as the singular and should not be limited to "only one" unless explicitly indicated to the contrary. Thus, for example, the use of "an acid" is intended to mean at least one acid.

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9%-11% and "about 2%" means 1.8%-2.2%).

The term "comprising" (and its grammatical variations) as used herein is used in the inclusive sense of "having" or "including" and not in the exclusive sense of "consisting only of".

"Keratin fiber" as used herein, includes, but is not limited to hair, such as hair on the human head and eyelashes.

"Volatile", as used herein, means having a flash point of less than about 100° C.

"Non-volatile", as used herein, means having a flash point of greater than about 100° C.

"Antioxidant" refers to a chemical compound, an enzyme or other organic molecule which prevents free radicals from causing oxidation of molecules in the body. Susceptible molecules include without limitation, such vital entities as DNA, RNA, lipids (fats), and proteins. The antioxidant, by reacting with the oxidant, protects these important molecules from being damaged. Examples of antioxidants include without limitation, vitamins A, C, E, carotenoids, polyphenols, and certain minerals.

"Substituted" as used herein, means comprising at least one substituent. Non-limiting examples of substituents include atoms, such as oxygen atoms and nitrogen atoms, as well as functional groups, such as acyloxyalky groups, carboxylic acid groups, amine or amino groups, acylamino groups, amide groups, halogen containing groups, ester groups, thiol groups, sulphonate groups, thiosulphate groups, siloxane groups, and polysiloxane groups. The substituent(s) may be further substituted.

The terms "organic compound" and "having an organic structure" mean compounds containing carbon atoms and hydrogen atoms and optionally heteroatoms such as S, O, N or P, alone or in combination.

As used herein, the terms "applying a composition onto keratin fibers" and "applying a composition onto hair" and variations of these phrases are intended to mean contacting the fibers or hair, with at least one of the compositions of the invention, in any manner.

As used herein, "formed from," means obtained from chemical reaction of, wherein "chemical reaction," includes spontaneous chemical reactions and induced chemical reactions. As used herein, the phrase "formed from," is open ended and does not limit the components of the composition to those listed.

The term "stable" as used herein means that the composition does not exhibit phase separation and/or crystallization.

The term "treat" (and its grammatical variations) as used herein refers to the application of the compositions of the present invention onto keratin fibers such as hair.

The terms "controlling" or "slowing down" (and its grammatical variations) as used herein include inhibiting hair color from penetrating into a keratin fiber such as hair; or inhibiting dye molecules or color-altering agents including but not limited to oxidative dyes, direct dyes, couplers, oxidation dye precursors, inorganic pigments, organic pigments, bleaching agents, lightening agents, lifting agents, or oxidizing agents from developing in their maximum capacity; or impeding dye molecules or color-altering agents from developing at a normal processing time by creating a film or coating barrier on a keratin fiber such as hair.

The terms "controlling" or "slowing down" (and its grammatical variations) as used herein also can refer to the reduction of the amount of color altering agent(s) that is deposited on or penetrate the hair fiber by creating a film barrier on a keratin fiber such as hair.

As used herein, the terms "method of controlling the coloration of hair," "method of slowing down the coloration of hair" or "method for controlling the variation in the artificial color of hair" is understood to mean any method for modifying the appearance of the keratin fibers or the hair with respect to their melanin or pigment or their artificial color. When the keratin fibers comprise hair on the human head, the term "method of controlling the coloration of hair," "method of slowing down the coloration of hair" or "method for controlling the variation in the artificial color of hair" is also understood to mean any method for coloring or dyeing or pigmenting or otherwise altering the shade of the hair.

The compositions and methods of the present invention can comprise, consist of, or consist essentially of the essential elements and limitations of the invention described herein, as well as any additional or optional ingredients, components, or limitations described herein or otherwise useful.

Unless otherwise specified herein, all percentages and ratios of components are by weight relative to the total weight of the final composition.

In an embodiment, the present invention relates to an acidic hair pretreatment composition, comprising:
 a) from about 12% to about 70% by weight of active material weight of active material, of coconut water;
 b) from about 1% to about 15% by weight of at least one antioxidant;
 c) optionally, at least one cosmetically acceptable carrier; and
wherein the pH of the composition is from about 2 to about 6; all weights being relative to the total weight of the composition.

In an embodiment, the present invention relates to a method of coloring hair, said method comprising:
 (1) applying onto hair, an acidic pretreatment hair composition comprising:
   a) from about 15% to about 50% by weight of active material, of coconut water;
   b) from about 1.5% to about 10% by weight of at least one antioxidant;
   c) optionally, at least one cosmetically acceptable carrier; and
wherein the pH of the composition is from about 2 to about 6; all weights being relative to the total weight of the composition; and
 (2) applying onto the hair, a hair color altering composition.

In an embodiment, the present invention relates to a method of coloring hair, said method comprising:
 (1) applying onto hair, an acidic pretreatment hair composition comprising:
   a) from about 18% to about 30% by weight of active material, of coconut water;
   b) from about 1% to about 8% by weight of at least one antioxidant;
   c) optionally, at least one cosmetically acceptable carrier; and
wherein the pH of the composition is from about 2 to about 6; all weights being relative to the total weight of the composition; and
 (2) applying onto the hair, a hair color altering composition.

In an embodiment, the present invention relates to an acidic pretreatment hair composition for controlling or slowing down the coloration of hair, the composition comprising:

a) from about 15% to about 50% by weight of active material, of coconut water;
b) from about 1% to about 8% by weight of at least one antioxidant;
c) at least one cosmetically acceptable carrier; and
wherein the pH of the composition is from about 2 to about 6; all weights being relative to the total weight of the composition.

In one embodiment, the present invention relates to a method for controlling or slowing down the coloration of hair, the method comprising:
(1) applying onto hair, an acidic pretreatment hair composition, comprising:
  a) from about 18% to about 30% by weight of active material, of coconut water;
  b) from about 0.5% to about 20% by weight of at least one antioxidant;
  c) optionally, at least one cosmetically acceptable carrier; and
wherein the pH of the composition is from about 2 to about 6; all weights being relative to the total weight of the composition; and
(2) applying onto the hair, a hair color altering composition.

In one embodiment, the present invention relates to a method for controlling the variation in the artificial color of hair, the method comprising:
(1) applying onto the mid-shaft up to the ends of the hair, an acidic pretreatment hair composition, comprising:
  a) from about 18% to about 30% by weight of active material, of coconut water;
  b) from about 1% to about 15% by weight of at least one antioxidant;
  c) optionally, at least one cosmetically acceptable carrier; and
wherein the pH of the composition is from about 2 to about 6; all weights being relative to the total weight of the composition; and
(2) applying onto the roots up to the ends of the hair, a hair color altering composition.

In another embodiment, the present invention relates to a kit comprising:
(1) an individually packaged hair pretreatment composition comprising:
  a) from about 12% to about 70% by weight of active material, of coconut water;
  b) from about 1% to about 8% by weight of at least one antioxidant;
  c) optionally, at least one cosmetically acceptable carrier; and
  wherein the pH of the composition is from about 2 to about 6; all weights being relative to the total weight of the composition;
(2) an individually packaged composition comprising a color-altering agent selected from oxidative dye precursors, direct dyes, pigments, lightening agents, bleaching agents, oxidizing agents, and mixtures thereof; and
(3) optionally, an individually packaged composition comprising at least one oxidizing agent.

In one embodiment, the present invention relates to a system for controlling the coloration of hair, the system comprising:
(1) an acidic hair pretreatment composition comprising:
  a) from about 15% to about 50% by weight of active material, of coconut water;
  b) from about 1% to about 10% by weight of at least one antioxidant;
  c) optionally, at least one cosmetically acceptable carrier; and
  wherein the pH of the composition is from about 2 to about 6; all weights being relative to the total weight of the composition;
(2) a composition comprising a color-altering agent selected from oxidative dye precursors, direct dyes, pigments, lightening agents, bleaching agents, oxidizing agents, and mixtures thereof; and
(3) optionally, a composition comprising at least one oxidizing agent.

In another embodiment, the present invention relates to a method of making an acidic pretreatment composition for application on the hair comprising:
(1) combining
  a) from about 15% to about 50% by weight of active material, of coconut water;
  b) from about 0.5% to about 20% by weight of at least one antioxidant;
  c) optionally, at least one cosmetically acceptable carrier; and
  wherein the pH of the composition is from about 2 to about 6; all weights being relative to the total weight of the composition; and
(2) mixing the components in (1) until uniformly distributed.

In certain embodiments, the compositions in the above described methods further comprise at least one auxiliary ingredient selected from at least one propellant, at least one emulsifier, at least one rheology modifier, at least one conditioner, at least one film forming polymer, at least one non film forming polymer, and mixtures thereof.

In other embodiments, the compositions and the compositions in the above described methods are in the form of aqueous hair cosmetic compositions such as liquids, gels, lotions or creams.

In other embodiments, the compositions and the compositions in the above described methods are in the form of sprays. The sprays may be both aerosol and non-aerosol.

In other embodiments, the compositions and the compositions in the above described methods are in the form of hair mousse cosmetic compositions.

In some embodiments, the at least one antioxidant is sodium metabisulfite.

In some embodiments, the at least one antioxidant is erythorbic acid.

In certain embodiments, the at least one antioxidant may be used in combination with a second antioxidant.

In other embodiments, the at least one antioxidant comprises both sodium metabisulfite and erythorbic acid.

In an embodiment, the optionally at least one cosmetically acceptable carrier is water.

In certain embodiments, the cosmetic composition in any one of the above-described methods is for controlling or slowing down the coloration of hair, or for controlling the variation in the artificial color of hair.

The methods according to various exemplary embodiments of the present invention may also provide improved and/or increased ease of uniform color deposit or a more uniform overall hair color from root to ends.

It should be understood that the precise numerical values used in the specification, including the examples and claims, form additional embodiments of the invention, and are intended to include any ranges which can be narrowed to any to end points disclosed within the exemplary ranges and values provided. Efforts have been made to ensure the accuracy of the numerical values disclosed. However, any measured value can inherently contain certain errors resulting from the standard deviation found in its respective measuring technique.

Coconut Water

As described herein, exemplary compositions according to the disclosure may comprise water extracted from Coconut (*Cocus nucifera*). In certain embodiments, the coconut water is present in an amount ranging from about 10% to about 80% by weight of active material, such as about 12% to about 70% by weight of active material, such as about 14% to about 60% by weight of active material, such as about 15% to about 50% by weight of active material, such as about 17% to about 40% by weight of active material or about 18% to about 30% by weight of active material, relative to the total weight of the composition, including all ranges and subranges there between.

According to various exemplary embodiments of the disclosure, the coconut water is present in an amount ranging from about 18% to about 30% by weight of active material, relative to the total weight of the composition.

The term "active material" as used herein to the refers to the amount of coconut water based on the percent activity of the raw material containing coconut water.

Coconut water is the water that is in the middle of the coconut. As coconut fruit matures, the water "dries up" or is utilized by the plant/fruit. Coconut water used in the present invention may be in liquid, powder, or freeze-dried form. Coconut water or the concentrate thereof is believed to provide superior efficacy compared to extracts, concentrates, or oils of other parts of the coconut and/or coconut tree, i.e. the fruit, milk, shell, seed, leaf, and bark.

In certain embodiments, the compositions of the present invention employ a raw material containing coconut water wherein the raw material is 98% active coconut water.

Coconut water contains the enzyme catalase-peroxidase. Not to be bound by any particular theory, it is believed the enzyme catalase-peroxidase contained in the coconut water is a hydrogen donor which reacts with hydrogen peroxide present in permanent and other reactive hair dye compositions to release oxygen. The foregoing reaction inhibits the uptake of the hair dye into the keratin fiber and slows down the hair dying or coloration process.

Antioxidant

As described herein, exemplary compositions according to the disclosure may comprise at least one antioxidant. In certain embodiments, the at least one antioxidant is present in an amount ranging from about 0.5% to about 20% by weight, such as about 0.5% to about 18% by weight, such as about 1% to about 15% by weight, such as about 1.5% to about 10% by weight, such as about 1% to about 8% by weight, relative to the total weight of the composition, including all ranges and subranges there between.

Examples of active agents or antioxidants include free-radical scavengers, keratolytic agents, vitamins (e.g., Vitamin E and derivatives thereof), anti-elastase and anti-collagenase agents, peptides, fatty acid derivatives, steroids, trace elements, extracts of algae and of planktons, enzymes and coenzymes, flavonoids and ceramides, hydroxy acids and mixtures thereof, and enhancing agents. These ingredients may be soluble or dispersible in whatever phase or phases is/are present in the cosmetic composition (i.e., aqueous and/or fatty (oil) phase.)

Mention may more particularly be made, as antioxidants, of tocopherol and its esters, in particular tocopheryl acetate; EDTA; sodium metabisulfite; erythorbic acid, ascorbic acid and its derivatives, in particular magnesium ascorbyl phosphate and ascorbyl glucoside; chelating agents, such as BHT, BHA or N,N'-bis(3,4,5-trimethoxybenzyl)ethylenediamine and its salts, and their mixtures.

In some embodiments, the antioxidants are present in an amount ranging from about 0.5% to about 20% by weight, such as about 0.5% to about 15% by weight, such as about 0.5% to about 10% by weight, such as about 1% to about 8% by weight, such as about 1% to about 5% by weight, relative to the weight of the composition, including all ranges and subranges there between. By way of non-limiting example, the amount of antioxidants may be about 0.5%, about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 9%, about 10%, about 11%, about 12%, about 13% about 14%, about 15%, about 16%, about 17%, about 18%, about 19%, or about 20%, by weight, relative to the total weight of the composition In some embodiments, at least two antioxidants are present in the compositions of the invention.

In certain embodiments, the at least one antioxidant is sodium metabisulfite and may be used in combination with a second antioxidant.

In further embodiments, the at least one antioxidant is erythorbic acid and may be used in combination with a second antioxidant.

In other embodiments, the at least one antioxidant comprises both sodium metabisulfite and erythorbic acid.

In certain embodiments, when there are at least two antioxidants in the compositions of the invention, the antioxidants are present in a combined amount ranging from about 0.5% to about 20% by weight, such as about 0.5% to about 18% by weight, such as about 1% to about 15% by weight, such as about 1.5% to about 10% by weight, such as about 2% to about 8% by weight, relative to the weight of the composition, including all ranges and subranges there between. By way of non-limiting example, the combined amount of antioxidants may be about 0.5%, about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 9%, about 10%, about 11%, about 12%, about 13% about 14%, about 15%, about 16%, about 17%, about 18%, about 19%, or about 20%, by weight, relative to the total weight of the composition.

In at least one exemplary embodiment, the combined amount of antioxidant is less than about 10% by weight, such as less than about 8% by weight, relative to the total weight of the composition.

Cosmetically Acceptable Carrier

The compositions of the present invention may optionally contain a cosmetically acceptable carrier. The cosmetically acceptable carrier can be present in the compositions of the present invention in the amount of about 95%, 90%, 80%, 70%, 60%, 50%, 40%, 30%, 20%, 10%, 5% by weight or less, relative to the total weight of the compositions. Additionally, the cosmetically acceptable carrier can be present in the compositions of the present invention in the amount of from about 1% to about 95% by weight, or from about 5% to about 90% by weight, or from about 20% to about 90% by weight, or from about 50% to about 90% by weight, relative to the weight of the compositions.

Useful cosmetically acceptable carriers include, but are not limited to, one or more aqueous systems, glycerin, C1-4 alcohols, organic solvents, fatty alcohols, fatty ethers, fatty esters, polyols, glycols, vegetable oils, mineral oils, liposomes, laminar lipid materials, silicone oils, water, or any combinations thereof.

As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol.

Other suitable examples of organic solvents are ethylene glycol, propylene glycol, butylene glycol, hexylene glycol, propane diol, and glycerin.

The organic solvents for use in the present invention can be volatile or non-volatile compounds.

The cosmetic compositions of the present invention can comprise other compounds constituting the cosmetically acceptable carrier. This cosmetically acceptable carrier may comprise water, a mixture of water and at least one cosmetically acceptable organic solvent, or at least one cosmetically acceptable organic solvent.

In certain embodiments, it is preferred that the amount of nonvolatile organic solvent/compound does not exceed 40% by weight, relative to the weight of the composition of the present invention.

In other certain embodiments, it is preferred that the amount of nonvolatile organic solvent/compound does not exceed 20% by weight, relative to the weight of the composition of the present invention.

In yet other certain embodiments, it is preferred that the amount of nonvolatile organic solvent/compound does not exceed 10% by weight, relative to the weight of the composition of the present invention.

In preferred embodiments of the present invention, the at least one cosmetically acceptable carrier is chosen from ethanol, glycol ether, for example, dipropylene glycol n-butyl ether, known under the tradename of DOWANOL DPnB, isododecane, mineral oil, propylene glycol, pentylene glycol, hexylene glycol, glycerol, and mixtures thereof.

In certain embodiments of the present invention, the at least one cosmetically acceptable carrier is chosen from ethylene glycol, propylene glycol, butylene glycol, hexylene glycol, propane diol, glycerin, and mixtures thereof.

In certain embodiments of the present invention, the at least one cosmetically acceptable carrier is chosen from ethanol.

In certain embodiments of the present invention, the at least one cosmetically acceptable carrier is chosen from water.

In yet some other embodiments, water that is not added as a separate ingredient, by itself, into the compositions of the present invention, such that water is present in the compositions of the present invention when it accompanies one or more ingredients of a raw material that is added into the composition invention.

In addition, the vehicle of the compositions according to the present invention can be in the form of a homogeneous phase formulation or in the form of an emulsion including, but not limited to, oil-in-water, water-in-oil and multiple including triple, phase emulsions. These emulsions can cover a broad range of consistencies including thin lotions (which can also be suitable for spray or aerosol delivery), creamy lotions, light creams and heavy creams. Other suitable topical carriers include anhydrous liquid solvents such as oil and alcohol; aqueous-based single phase liquid solvent (e.g., hydro-alcoholic solvent system); anhydrous solid and semi-solid (such as gel and stick); and aqueous based gel and mousse system.

pH

In some embodiments, the pH of the compositions employed in the methods of the present invention ranges from about 2 to about 6, or preferably from about 2 to about 5, or more preferably from about 2.5 to about 4.5, including all ranges and subranges there between.

In certain embodiments, the pH of the compositions employed in the methods of the present invention is at about 3.8.

The pH of the composition of the present invention may be adjusted to the desired value using conventional acidifying or basifying agents.

All numbers expressing pH values are to be understood as being modified in all instances by the term "about" which encompasses up to +/−3%.

Auxiliary Ingredients

The compositions of the present invention can also comprise auxiliary ingredients, for instance those chosen from the non-exhaustive list such as propellants, emulsifiers, rheology modifiers and film forming agents such as film forming polymers, non-film forming polymers, humectants, conditioning agents, plasticizers, coalescers, fillers, dyes such as oxidative dyes and direct dyes, waxes, surfactants, preserving agents, oils such as mineral, organic or plant oils, fragrances, anti-oxidants, sunscreens, sequestering agents, softeners, anti-foams, basifying agents, wetting agents, spreading agents, dispersants, pigments, proteins, ceramides, vitamins, clays, colloidal minerals, nacreous agents, peptizers, preserving agents, reducing agents, oxidizing agents, pH adjusters, silicones, plant extracts, paraffins, fatty acids, and mixtures thereof.

The person skilled in the art will ensure that any auxiliary ingredient and their amounts are selected in such a way as to cause no detriment to the properties of the compositions disclosed herein.

The at least one auxiliary ingredient may be present in an amount ranging from 0.001% to 50% by weight, relative to the total weight of the entire composition, including all ranges and subranges there between.

In some embodiments, the compositions of the present invention may contain at least one film forming polymer chosen from all the anionic, cationic, amphoteric and non-ionic film forming polymers and mixtures thereof.

In certain embodiments, the compositions of the present invention may contain at least one emulsifier.

Emulsifiers or dispersing agents, include, without limitation, any which are compatible with the solvent and ingredients used in the composition of the present invention. The emulsifying agents which can be used according to the invention are those having an HLB of less than 7 and in particular fatty acid esters of polyols such as mono-, di-, tri- or sesqui-oleates or -stearates of sorbitol or glycerol, laurates of glycerol or polethylene glycol; alkyl or alkoxy dimethicone copolyols having an alkyl or alkoxy chain pendent or at the end of a silicone-based backbone having for example from 6 to 22 carbon atoms. The emulsifying agents may also be those having an HLB greater than 7 such as fatty acid esters of polyethylene glycol (monostearate or monolaurate of polyethylene glycol); esters of fatty acids (stearate, oleate) of sorbitol which are polyoxyethylenated; polyoxy ethylenated alkyl (lauryl, cetyl, stearyl, octyl)ethers and dimethicone copolyols. In general, it is possible to use nonionic or anionic or cationic emulsifiers well known to persons skilled in the art.

The nonionic type emulsifiers are fatty acids or amides of polyalkoxylated and/or polyglycerolated fatty acids; polyoxyethylenated and/or polyoxypropylenated fatty alcohols (i.e., compounds prepared by reacting an aliphatic fatty alcohol such as behenyl or cetyl alcohol with ethylene oxide or propylene oxide or an ethylene oxide/propylene oxide mixture); fatty acid esters of polyols, optionally polyoxyethylenated and/or polyoxypropylenated (i.e., compounds prepared by reacting a fatty acid such as stearic acid or oleic acid with a polyol such as, for example, an alkylene glycol or glycerol or a polyglycerol, optionally in the presence of ethylene oxide or propylene oxide or an ethylene oxide/propylene oxide mixture); and polyalkoxylated and/or polyglycerolated alkylphenols; or polyalkoxylated and/or polyglycerolated 1,2- or 1,3-alkanediols; and alkylethers of polyalkoxylated and/or polyglycerolated 1,2- or 1,3-alkanediols or alkenediols, or mixtures thereof.

The esters of fatty acids and polyoxyethylenated polyols for which the polyol is sorbitol are known products (Polysorbate and products sold under the mark "Tween").

The emulsifiers according to the invention can also be anionic surfactants which may have a hydrophilic-lipophilic balance (HLB) ranging from 10 to 40. They are principally salts of fatty acids (for example alkaline salts or organic salts such as amine salts), the said fatty acids having, for example, from 12 to 18 carbon atoms and being able to have a double bond as in the case of oleic acid; the alkaline salts or salts of organic bases of alkyl-sulfuric and alkyl-sulfonic acids having 12 to 18 carbon atoms, of alkyl-arylsulfonic acids whose alkyl chain contains 6 to 16 carbon atoms, the aryl group being, for example, a phenyl group. They are also ether-sulfates, in particular, the sulfatation products of fatty alcohols and polyalkoxylated alkylphenols, in which the aliphatic chain has from 6 to 20 carbon atoms and the polyalkoxylated chain has from 1 to 30 oxyalkylene units, in particular oxyethylene, oxypropylene or oxybutylene. All these anionic surfactants are well known and many among them are commercial products.

The emulsifiers according to the invention can also be cationic surfactants such as quaternary ammonium derivatives.

Particularly preferred emulsifying agents are Isoceteth-20, Polysorbate 20, PEG-40 hydrogenated castor oil, oleth-2, laureth-7, cetyl alcohol, glyceryl stearate, and mixtures thereof.

The emulsifiers may be present in the composition of the present invention in an amount of from 0.05% to 10% by weight, preferably in an amount of from 0.1 percent to 5% by weight, and more preferably in an amount of from 0.5% to 3.0% by weight, based on the total weight of the composition.

The emulsifiers may be employed in the compositions of the present invention in order to solubilize fatty substances such as fragrance oils or esters, whenever said fatty substances are additionally present in the compositions.

In other embodiments, the compositions of the present invention may contain at least one rheology modifier (also called rheology-modifying agent).

Broadly, the rheology modifier(s) that may be useful in the practice of the present invention include those conventionally used in cosmetics such as polymers of natural origin and synthetic polymers. Rheology modifiers are employed in the compositions of the present invention when it is desired to adjust the viscosity or thickness of the compositions or to achieve a particular composition texture.

Representative rheology-modifying agents that may be used in the practice of the present invention are those other than the at least one film forming polymer of the present invention and include nonionic, anionic, cationic, and amphoteric polymers, and other rheology modifiers such as cellulose-based thickeners (e.g., hydroxyethylcellulose, hydroxypropylcellulose, carboxymethylcellulose, cationic cellulose ether derivatives, quaternized cellulose derivatives, etc.), guar gum and its derivatives (e.g., hydroxypropyl guar, cationic guar derivatives, etc.), gums such as gums of microbial origin (e.g., xanthan gum, scleroglucan gum, etc.), and gums derived from plant exudates (e.g., gum arabic, ghatti gum, karaya gum, gum tragacanth, carrageenan gum, agar gum and carob gum), pectins, alginates, and starches, crosslinked homopolymers of acrylic acid or of acrylamidopropane-sulfonic acid, associative polymers, non-associative thickening polymers, and water-soluble thickening polymers.

In some embodiments, the rheology-modifying agent includes a polymer other than the at least one film forming polymer of the present invention and chosen from nonionic, anionic, cationic and amphoteric amphiphilic polymers.

The rheology-modifying agents may also be chosen from associative celluloses include quaternized cationic celluloses and quaternized cationic hydroxyethylcelluloses modified by groups containing at least one hydrophobic chain, such as alkyl, arylalkyl or alkylaryl groups containing at least 8 carbon atoms, and mixtures thereof.

The alkyl radicals carried by the above quaternized celluloses or hydroxyethylcelluloses may, in various embodiments, comprise from 8 to 30 carbon atoms. The aryl radicals may, for example, denote the phenyl, benzyl, naphthyl or anthryl groups. Representative examples of quaternized alkylhydroxy-ethylcelluloses containing a C8-C30 hydrophobic chain include the products Quatrisoft LM 200®, Quatrisoft LM-X 529-18-A®, Quatrisoft LM-X 529-18B® (C12 alkyl) and Quatrisoft LM-X 529-8® (Ci8 alkyl) sold by Amerchol and the products Crodacel QM®, Crodacel QL® (C12 alkyl) and Crodacel QS® (Ci8 alkyl) sold by Croda.

Representative examples of nonionic cellulose derivatives include hydroxyethylcelluloses modified by groups comprising at least one hydrophobic chain, such as alkyl, arylalkyl or alkylaryl groups, or their blends, and in which the alkyl groups are, for example, C8-C22 alkyl groups, such as the product Natrosol Plus Grade 330 CS® (C16 alkyls) sold by Aqualon or the product Bermocoll EHM 100® sold by Berol Nobel.

Representative examples of cellulose derivatives modified by alkylphenyl polyalkylene glycol ether groups include the product Amercell Polymer HM-1500® sold by Amerchol.

The rheology-modifying agent is typically present in an amount ranging from about 0.01% to about 10% by weight, in some embodiments from about 0.1% to about 5% by weight, or from about 0.5% to about 1% by weight, based on the total weight of the composition.

In some instances, certain rheology modifiers are also known as gelling agents or thickening agents.

In yet other embodiments, the compositions of the present invention may contain at least one propellant. Propellants can used to deliver the composition as a foam (such as in a mousse or foam product).

Representative examples of propellants include C3 to C5 alkanes such as n-butane, isobutane, isopropane, and propane, dimethyl ether, C2-C5 halogenated hydrocarbons, e.g., 1,1-difluoroethane or hydroflurocarbon, difluoroethane, chlorodifluoroethane, chlorodifluoromethane, air (such as compressed air), nitrogen, carbon dioxide, and mixtures thereof. The amount of the propellant can range from about 3 to about 90%, and in some embodiments from about 3 to about 60%, by weight, or such as from about 3 to about 20% by weight, or such as from about 3 to about 10% by weight, or such as from about 3 to about 6%, by weight based on the total weight of the composition, including all ranges and subranges there between.

The compositions in the methods of the present invention may be formulated in any suitable product form. Such product forms include, but are not limited to, aerosol spray, cream, dispersion, emulsion, foam, gel, liquid, lotion, mousse, ointment, patch, pomade, powder, pump spray, solid, solution, stick, tonic, and towelette. The compositions may also be provided as rinse-off or leave-in products, preferably, rinse-off products.

In one particular embodiment, the composition of the present invention is in the form of a liquid.

In another particular embodiment, the composition of the present invention is in the form of a cream.

In another particular embodiment, the composition of the present invention is in the form of a gel.

In some other embodiments, the cosmetically acceptable carrier in the composition of the present invention comprises at least one volatile organic solvent or compound (VOC) (e.g., in the case of a spray or an aerosol spray). To reduce the amount of VOC (low VOC product), the volatile organic solvent or compound is partially replaced with water. The amount of the volatile organic solvent generally ranges from greater than 0 (e.g., about 0.01%) to about 90%, and in some embodiments from greater than 0 to about 55%, and in some embodiments from greater than 0 to about 2%, by weight, based on the total weight of the composition. It is preferred that the amount of volatile organic solvent does not exceed 55% by weight.

The compositions of the present invention may be packaged, for example, in a bottle, a spray device such as an aerosol container/can, a pump dispenser or pump spray, a jar, such as those customary in cosmetology.

The compositions may be applied onto keratin fibers by using the fingers or hand, or by use of a suitable applicator or by directly dispensing the compositions from a device.

Methods of Making

The compositions of the present invention are made by combining coconut water and at least one antioxidant.

In one embodiment, the method of making the acidic pretreatment composition of the present invention comprises the steps of:
(1) combining
  a) from about 10% to about 80% by weight of active material, of coconut water;
  b) from about 0.5% to about 20% by weight of at least one antioxidant;
  c) optionally, at least one cosmetically acceptable carrier; and
wherein the pH of the composition is from about 2 to about 6; all weights being relative to the total weight of the composition; and
(2) mixing the foregoing components in (1) until uniformly distributed.

In an embodiment, coconut water is first combined with at least one cosmetically acceptable carrier. The resulting mixture is then combined with one or more of the antioxidants of the pretreatment composition of the invention.

In another embodiment, the coconut water is combined with the antioxidants and directly applied to the keratinous fibers.

Methods of Use

Embodiments disclosed herein are methods for coloring the hair, or for controlling/slowing down the coloration of hair or controlling the variation in the artificial color of hair, or kits or systems thereof, involving applying onto hair, any one of the compositions disclosed herein.

The compositions of the present invention may be employed in an effective amount to adequately cover the surface of the selected or isolated fibers of the hair and to achieve the desired cosmetic effect such as uniform hair color from root to tip, multi-toned or multi-colored hair, highlights, lowlights, or satisfactory gray coverage. The precise amount of composition to be applied onto the hair will thus depend on the degree of treatment desired.

Thus, in one embodiment, the present invention relates to a method of coloring hair, said method comprising:
(1) applying onto hair, an acidic pretreatment hair composition comprising:
  a) from about 10% to about 80% by weight of active material, of coconut water;
  b) from about 0.5% to about 20% by weight of at least one antioxidant;
  c) optionally, at least one cosmetically acceptable carrier; and
wherein the pH of the composition is from about 2 to about 6; all weights being relative to the total weight of the composition; and
(2) applying onto the hair, a hair color altering composition.

In another embodiment, the present invention relates to a method for slowing down the coloration of hair, the method comprising:
(1) applying onto hair, an acidic pretreatment hair composition, comprising:
  a) from about 10% to about 80% by weight of active material, of coconut water;
  b) from about 0.5% to about 20% by weight of at least one antioxidant;
  c) optionally, at least one cosmetically acceptable carrier; and
wherein the pH of the composition is from about 2 to about 6; all weights being relative to the total weight of the composition; and
(2) applying onto the hair, a hair color altering composition.

In a third embodiment, the present invention relates to a method for controlling the variation in the artificial color of hair, the method comprising:
(1) applying onto the mid-shaft up to the ends of the hair, an acidic pretreatment hair composition, comprising:
  a) from about 10% to about 80% by weight of active material, of coconut water;
  b) from about 0.5% to about 20% by weight of at least one antioxidant;
  c) optionally, at least one cosmetically acceptable carrier; and
wherein the pH of the composition is from about 2 to about 6; all weights being relative to the total weight of the composition; and
(2) applying onto the roots up to the ends of the hair, a hair color altering composition.

The hair color altering composition that may be applied after contacting the hair with the pretreatment composition comprises at least one color-altering agent selected from oxidative dyes, direct dyes, couplers, oxidation dye precursors, pigments, lightening agents, lifting agents, bleaching agents, oxidizing agents, and mixtures thereof.

Thus, the hair color altering composition may be a permanent hair dye product, a semi-permanent hair dye product, a demi-permanent hair dye product, a bleach product, a temporary dye product, or a hair lightening or highlighting product.

The hair color altering composition may first be combined with a developer or oxidizing composition containing at least one oxidizing agent before application onto the hair. The least one oxidizing agent may be selected from perborates, peroxides, percarbonates, and mixtures thereof. One suitable example of an oxidizing agent chosen from peroxides is hydrogen peroxide.

Instructions for applying the compositions disclosed herein may comprise directions of use of the composition for the end-user to follow. The end-user may be a consumer or cosmetologist or salon hair dresser. Directions may comprise instructing the end-user to take an amount of the composition in sufficient quantity such that the composition adequately covers the selected hair fibers and imparts the desired color or tone to the hair fibers. Directions may also comprise instructing the end-user to apply the pretreatment composition from mid-shaft of the hair or from the visible demarcation line between new hair growth and previously artificially colored hair down to the ends/tips of the hair. Directions may additionally instruct the end-user to use a device such as a foil, comb, brush (e.g., hair color brush or brush wand), flat iron plates or the fingers for separating the fibers of the hair.

It has been surprisingly and unexpectedly discovered that the methods of the present invention resulted in a uniform overall color from root to tip of the hair, as well as satisfactory gray coverage. The pretreatment composition is also beneficial for multi-toned or multi-colored hair, highlight or low-light treatments.

The efficacy of the pretreatment compositions on the hair may be evaluated by assessing (whether visually or by a measuring device) the appearance and color of the hair after contacting the hair with the pretreatment composition of the invention, followed by application of a hair color altering composition onto the hair, rinsing both compositions and allowing the hair to dry naturally or drying the hair with a blow dryer.

As used herein, the method and composition disclosed herein may be used on the hair that has not been artificially dyed, pigmented or permed or on the hair that has been artificially dyed, pigmented or permed.

Examples

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result.

The following Examples are intended to be non-restrictive and explanatory only, with the scope of the invention being defined by the claims.

The ingredient amounts/concentrations in the compositions/formulas described below are expressed in % by weight, based on the total weight of the composition/formula.

| INVENTIVE COMPOSITION: Formula A | |
|---|---|
| Raw Material | Amount |
| WATER | Q.S. |
| XANTHAN GUM | 1.00 |
| SODIUM METABISULFITE | 1.50 |
| ERYTHORBIC ACID | 1.00 |
| GLYCERIN | 3.00 |

-continued

| INVENTIVE COMPOSITION: Formula A | |
|---|---|
| Raw Material | Amount |
| PROPYLENE GLYCOL | 5.00 |
| COCOS NUCIFERA (COCONUT) WATER (98% active) | 19.6 |
| POLYQUATERNIUM-39 (9.25% active) | 0.0925 |
| TOTAL: | 100.00 |
| PH: | 3.85 |

The formula above was made according to this method of preparation:

1. Add xanthan gum to the water and mix at 300-500 RPM for 15 minutes.
2. Add glycerin and continue to mix for 5 minutes.
3. Add propylene glycol and continue to mix for 5 minutes.
4. Add polyquaternium-39 and continue to mix for 5 minutes.
5. Add erythorbic acid and sodium metabisulfite and continue to mix for 5 minutes.
6. Add *Cocos Nucifera* (coconut) water and continue to mix for 5 minutes.
7. Add citric acid to adjust the pH between 2-6.

Example 2

Colorimetric Measurements for Color Deposit on Hair Swatches

The Minolta CM2600d spectrocolorimeter (specular components included, 10 degrees angle, illuminant D65) in the CIEL*a*b* system was used for measuring the degree of color deposit on hair, Thus, the L parameter L was measured. L* represents the intensity of the color. The greater the value of L, the lighter or less intense the color. Conversely, the lower the value of L, the darker or more intense the color (this can also indicate greater color deposit when the composition contains colorants).

ΔL or the difference between the L value for the treated hair versus the L value for the control hair swatch can also be measured. ΔL represents a change in the value of L: the more negative the ΔL value is, the darker the color that is deposited on the hair: Δ L=Lt (treated hair)–Lc (control hair).

Comparative Examples

TABLE 1

| COMPARATIVE EXAMPLES ON UNPERMED HAIR | | | |
|---|---|---|---|
| | Shade | 90% Gray Hair Type | L* |
| Comparative Example 1 | Virgin hair | Unpermed | 59.96 |
| Comparative Example 2 | Chromatics 6.54 - brown/copper | Unpermed | 25.02 |
| Comparative Example 3 | Pref. 6.45 - auburn | Unpermed | 23.49 |
| Comparative Example 4 | Pref. 4R - dark auburn | Unpermed | 24.68 |

TABLE 2

COMPARATIVE EXAMPLES ON PERMED HAIR

| | Shade | 90% Gray Hair Type | L* |
|---|---|---|---|
| Comparative Example 5 | Virgin | Permed | 59.96 |
| Comparative Example 6 | Chromatics 6.54 - brown/copper | Permed | 21.23 |
| Comparative Example 7 | Pref. 6.45 - auburn | Permed | 24.56 |
| Comparative Example 8 | Pref. 4R - dark auburn | Permed | 26.14 |

The above described Comparative Examples 2-4 are hair swatches that were colored using a standard (typical) hair color on unpermed hair, without pre-treating the hair with the inventive composition. Comparative Examples 6-8 are hair swatches that were permed and then colored using a standard (typical) hair color, without pre-treating the hair with the inventive composition. Comparative Example 1 is unpermed hair which has not been colored and which was not pre-treated with the inventive composition. Comparative Example 5 is permed hair which has not been colored and which was not pre-treated with the inventive composition.

TABLE 3

INVENTIVE COMPOSITION (FORMULA A) ON UNPERMED HAIR

| | Shade | 90% Gray Hair Type | L* |
|---|---|---|---|
| Inventive Example 1 | Virgin | Unpermed | 57.77 |
| Inventive Example 2 | Chromatics 6.54 - brown/copper | Unpermed | 32.15 |
| Inventive Example 3 | Pref. 6.45 - auburn | Unpermed | 34.56 |
| Inventive Example 4 | Pref. 4R - dark auburn | Unpermed | 37.15 |

TABLE 4

INVENTIVE COMPOSITION (FORMULA A) ON PERMED HAIR

| | Shade | 90% Gray Hair Type | L* |
|---|---|---|---|
| Inventive Example 5 | Virgin | Permed | 57.77 |
| Inventive Example 6 | Chromatics 6.54 - brown/copper | Permed | 36.15 |
| Inventive Example 7 | Pref. 6.45 - auburn | Permed | 37.28 |
| Inventive Example 8 | Pref. 4R - dark auburn | Permed | 39.15 |

The above described Inventive Examples 2-4 are hair swatches that were colored using a standard (typical) hair color on unpermed hair, after applying the inventive composition of Formula A onto the hair. Inventive Examples 6-8 are hair swatches that were permed and then colored using a standard (typical) hair color, after applying the inventive composition of Formula A onto the hair. Inventive Example 1 is unpermed hair which has not been colored but was contacted/treated with the inventive composition of Formula A. Inventive Example 5 is permed hair which has not been colored but was contacted/treated with the inventive composition of Formula A.

Testing on a Model's Hair

This test was conducted on a model with medium length natural level 6 hair color with approximately 50-75% gray hair. Her hair was divided into two sections. The left section was pre-treated with the Pre-Treatment composition (invention) and the right section was not treated with the pre-treatment composition.

The inventive compositions above tested by:
1. Apply 10 g of the inventive composition to the hair, application starting mid-shaft and going to the ends. Allow to process for 10 minutes. Do not rinse off.
2. Apply hair color product on the entire head of hair (including the hair section pre-treated with the inventive composition). Allow to process for 30 minutes.
3. Rinse out both the inventive composition and hair color product.

Observations:

After processing time was completed, both the hair color product and the inventive pretreatment composition were rinsed off the hair of the model and the hair was dried. The model was then taken to the light room for color evaluation. Evaluation showed that the section that was pre-treated with the inventive pretreatment composition was visibly uniform in color from roots to ends. This section looked more natural and was rich in color. The half of the head that was not pre-treated with the inventive pretreatment composition appeared over-processed and faded; especially the mid shaft and ends. Color Deposit was not uniform from roots to ends.

It will be apparent to those skilled in the art that various modifications and variations can be made in the delivery system, composition and methods of the invention without departing from the spirit or scope of the invention. Thus, it is intended that the present invention cover the modifications and variations of this invention provided that they come within the scope of the appended claims and their equivalents.

What is claimed is:

1. An acidic hair pretreatment composition, comprising:
   a) from about 10% to about 80% by weight of active material, of coconut water;
   b) from about 0.5% to about 20% by weight of at least one antioxidant;
   c) optionally, at least one cosmetically acceptable carrier; and
   wherein the pH of the composition is from about 2 to about 6; all weights being relative to the total weight of the composition.

2. The hair pretreatment composition of claim 1, wherein the coconut water (a) comprises catalase-peroxidase enzyme.

3. The hair pretreatment composition of claim 2, wherein the coconut water (a) is present in an amount of from about 18% to about 30% by weight of active material, relative to the total weight of the composition.

4. The hair pretreatment composition of claim 3, wherein the at least one antioxidant (b) is present in an amount of from about 1% to about 8% by weight, relative to the total weight of the composition.

5. The hair pretreatment composition of claim 4, wherein the at least one antioxidant (b) is selected from tocopherol, tocopheryl acetate, Ethylenediaminetetraacetic acid (EDTA), sodium metabisulfite, erythorbic acid, ascorbic acid, magnesium ascorbyl phosphate, ascorbyl glucoside, Butylated hydroxytoluene (BHT), Butylated hydroxyanisole (BHA), and mixtures thereof.

6. The hair pretreatment composition of claim 5, wherein the at least one antioxidant (b) comprises sodium metabisulfite and erythorbic acid.

7. The hair pretreatment composition of claim 5, wherein the optionally at least one cosmetically acceptable carrier (c) is chosen from volatile organic solvents, non-volatile organic solvents, water and mixtures thereof.

8. The hair pretreatment composition of claim 7, wherein the at least one cosmetically acceptable carrier (c) is present in an amount of from about 5% to about 90% by weight, relative to the total weight of the composition.

9. The hair pretreatment composition of claim 5, wherein the composition is a pretreatment composition for use before applying a hair color-altering composition comprising a color-altering agent selected from oxidative dyes, direct dyes, couplers, oxidation dye precursors, pigments, lightening agents, lifting agents, bleaching agents, oxidizing agents, and mixtures thereof.

10. The hair pretreatment composition of claim 5, wherein the composition is employed for controlling coloration of hair or alteration of the color of hair.

11. The hair pretreatment composition of claim 5, wherein the composition further comprises at least one auxiliary ingredient selected from propellants, emulsifiers, rheology modifiers, film forming agents, neutralizing agents, humectants, conditioning agents, plasticizers, coalescers, fillers, dyes, waxes, surfactants, preserving agents, oils, fragrances, sunscreens, sequestering agents, softeners, antifoams, basifying agents, wetting agents, spreading agents, dispersants, pigments, proteins, ceramides, vitamins, clays, colloidal minerals, nacreous agents, peptizers, preserving agents, reducing agents, oxidizing agents, pH adjusters, silicones, plant extracts, paraffins, fatty acids, and mixtures thereof.

12. A method of coloring hair, said method comprising
(1) applying onto hair, an acidic hair pretreatment composition comprising:
a) from about 10% to about 80% by weight of active material, of coconut water;
b) from about 0.5% to about 20% by weight of at least one antioxidant;
c) optionally, at least one cosmetically acceptable carrier; and
wherein the pH of the composition is from about 2 to about 6;
all weights being relative to the total weight of the composition; and
(2) applying onto the hair, a hair color altering composition.

13. The method of claim 12, wherein the method is for controlling the coloration of hair.

14. The method of claim 13, wherein the hair pretreatment composition applied in step (1) is left on the hair for a period of from about 1 minute to about 60 minutes.

15. The method of claim 14, wherein the hair pretreatment composition applied in step (1) is not rinsed off from the hair before step (2).

16. An acidic hair pretreatment composition for controlling or slowing down the coloration of hair, the composition comprising:
a) from about 18% to about 30% by weight of active material, of coconut water;
b) from about 1% to about 8% by weight of at least one antioxidant selected from tocopherol, tocopheryl acetate, Ethylenediaminetetraacetic acid (EDTA), sodium metabisulfite, erythorbic acid, ascorbic acid, magnesium ascorbyl phosphate, ascorbyl glucoside, Butylated hydroxytoluene (BHT), Butylated hydroxyanisole (BHA), and mixtures thereof;
c) optionally, at least one cosmetically acceptable carrier; and
wherein the pH of the composition is from about 2 to about 6;
all weights being relative to the total weight of the composition.

17. A method for slowing down the coloration of hair, the method comprising:
(1) applying onto hair, an acidic pretreatment composition, comprising:
a) from about 18% to about 30% by weight of active material, of coconut water;
b) from about 1% to about 8% by weight of at least one antioxidant selected from tocopherol, tocopheryl acetate, Ethylenediaminetetraacetic acid (EDTA), sodium metabisulfite, erythorbic acid, ascorbic acid, magnesium ascorbyl phosphate, ascorbyl glucoside, Butylated hydroxytoluene (BHT), Butylated hydroxyanisole (BHA), and mixtures thereof;
c) optionally, at least one cosmetically acceptable carrier; and
wherein the pH of the composition is from about 2 to about 6;
all weights being relative to the total weight of the composition; and
(2) applying onto the hair, a hair color altering composition.

18. A method for controlling the variation in the artificial color of hair, the method comprising:
(1) applying onto the mid-shaft up to the ends of the hair, an acidic pretreatment composition, comprising:
a) from about 12% to about 70% by weight of active material, of coconut water;
b) from about 1% to about 15% by weight of at least one antioxidant;
c) optionally, at least one cosmetically acceptable carrier; and
wherein the pH of the composition is from about 2 to about 6
all weights being relative to the total weight of the composition; and
(2) applying onto the roots up to the ends of the hair, a hair color altering composition.

19. A kit comprising:
(1) an individually packaged hair pretreatment composition comprising:
a) from about 10% to about 80% by weight of active material, of coconut water;
b) from about 1% to about 15% by weight of at least one antioxidant;
c) optionally, at least one cosmetically acceptable carrier; and
wherein the pH of the composition is from about 2 to about 6;
all weights being relative to the total weight of the composition;
(2) an individually packaged composition comprising a color-altering agent selected from oxidative dye precursors, direct dyes, pigments, lightening agents, bleaching agents, oxidizing agents, and mixtures thereof; and
(3) optionally, an initially packaged composition comprising at least one oxidizing agent.

20. A system for controlling the coloration of hair, the system comprising:
(1) an acidic hair pretreatment composition comprising:
a) from about 15% to about 50% by weight of active material, of coconut water;
b) from about 1% to about 10% by weight of at least one antioxidant;

c) optionally, at least one cosmetically acceptable carrier; and wherein the pH of the composition is from about 2 to about 6;

all weights being relative to the total weight of the composition;

(2) a composition comprising a color-altering agent selected from oxidative dye precursors, direct dyes, pigments, lightening agents, bleaching agents, oxidizing agents, and mixtures thereof; and (3) optionally, a composition comprising at least one oxidizing agent.

21. A method of making an acidic pretreatment composition for application to the hair comprising:

(1) combining
- a) from about 12% to about 70% by weight of active material, of coconut water;
- b) from about 1% to about 15% by weight of at least one antioxidant;
- c) optionally, at least one cosmetically acceptable carrier; and wherein the pH of the composition is from about 2 to about 6; all weights being relative to the total weight of the composition; and (2) mixing the components in (1) until uniformly distributed.

* * * * *